United States Patent [19]

Felix

[11] Patent Number: 4,535,181

[45] Date of Patent: Aug. 13, 1985

[54] N-CARBOALKOXYMETHYL-N-HALOMETHYL AMIDES

[75] Inventor: Raymond A. Felix, Richmond, Calif.

[73] Assignee: Stauffer Chemical Company, Westport, Conn.

[21] Appl. No.: 609,921

[22] Filed: May 14, 1984

Related U.S. Application Data

[63] Continuation of Ser. No. 468,223, Feb. 22, 1983, Pat. No. 4,482,504, which is a continuation-in-part of Ser. No. 412,624, Aug. 30, 1982, Pat. No. 4,425,284.

[51] Int. Cl.$^3$ ............................................. C07C 103/48
[52] U.S. Cl. .................................................... 560/172
[58] Field of Search ......................................... 560/172

[56] References Cited

U.S. PATENT DOCUMENTS 4,054,668 10/1977 Kirino ................................. 560/172

Primary Examiner—Michael L. Shippen
Attorney, Agent, or Firm—Edwin H. Baker

[57] ABSTRACT

A method of preparing N-phosphonomethylglycine comprising (a) reacting a substituted triazine with an acyl halide to form the N-carboalkoxymethyl-N-halomethyl amide of the acyl halide; reacting the said amide with a phosphite to form a phosphonate compound; and hydrolyzing said phosphonate to yield N-phosphonomethylglycine.

3 Claims, No Drawings

N-CARBOALKOXYMETHYL-N-HALOMETHYL AMIDES

CROSS REFERENCE TO RELATED APPLICATIONS

This is a continuation of application Ser. No. 468,223, filed Feb. 22, 1983, U.S. Pat. No. 4,482,504, which is a continuation-in-part application of application Ser. No. 412,624, filed Aug. 30, 1982 U.S. Pat. No. 4,425,284.

FIELD OF THE INVENTION

This invention is a new process for preparing N-phosphonomethylglycine.

BACKGROUND OF THE INVENTION

N-Phosphonomethylglycine and certain salts are particularly effective as post-emergence herbicides. The commercial herbicide is sold as a formulation containing the isopropylamine salt of N-phosphonomethylglycine.

N-Phosphonomethylglycine can be made by a number of methods. One such method, as described in U.S. Pat. No. 3,160,632 is to react N-phosphinomethylglycine (glycinemethylenephosphonic acid) with mercuric chloride in water at reflux temperature, and subsequently separating the reaction products. Other methods are phosphonomethylation of glycine and the reaction of ethyl glycinate with formaldehyde and diethylphosphite. The latter method is described in U.S. Pat. No. 3,799,758. In addition, there is a series of patents relating to the preparation of N-phosphonomethylglycine, including U.S. Pat. Nos. 3,868,407, 4,197,254 and 4,199,354.

Close prior art is U.S. Pat. No. 3,923,877, which teaches the reaction of 1,3,5-tricyanomethylhexahydro-1,3,5-triazine with excess disubstituted phosphite to form $(RO)_2P(O)CH_2NHCH_2CN$ (R is hydrocarbyl or substituted hydrocarbyl) which is hydrolyzed to yield N-phosphonomethylglycine.

Because of the commercial importance of N-phosphonomethylglycine and certain salts as herbicides, improved methods of preparing these compounds are valuable.

BRIEF DESCRIPTION OF THE INVENTION

This invention relates to a process for preparing N-phosphonomethylglycine which comprises:

(1) reacting 1,3,5-tricarboalkoxymethylhexahydro-1,3,5-triazine with an acyl halide, preferably acyl chloride to form the N-carboalkoxymethyl-N-halomethyl amide of the acyl halide;

(2) reacting the amide with a phosphite to form N-carboalkoxymethyl-N-acyl aminomethyl phosphonate; and (3) hydrolyzing this phosphonate to yield N-(phosphonomethyl)glycine.

DETAILED DESCRIPTION OF THE INVENTION

The process of this invention may be illustrated by the following reaction scheme:

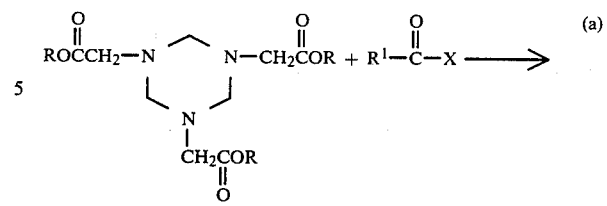

wherein R and $R^1$ are an aliphatic or aromatic group as defined hereinafter, preferably $C_1$-$C_4$ alkyl, most preferably methyl or ethyl and X is chlorine, bromine, or iodine, preferably chlorine.

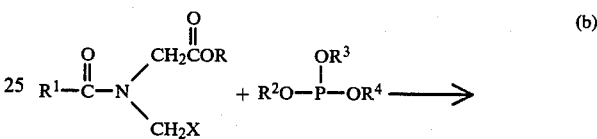

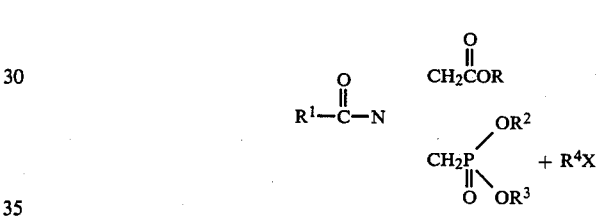

wherein R, $R^1$ and X are defined as above and $R^2$ and $R^3$ are both aromatic groups or both aliphatic group, preferably $R^2$ and $R^3$ are $C_1$-$C_6$ alkyl, more preferably $C_1$-$C_4$ alkyl, and $R^4$ is an aliphatic group, preferably $R^4$ is $C_1$-$C_6$ alkyl, more preferably $C_1$-$C_4$ alkyl or $R^4$ is an alkali metal (M), preferably sodium or potassium.

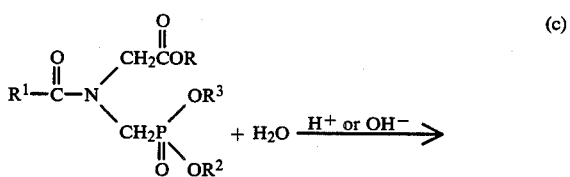

wherein R, $R^1$, $R^2$ and $R^3$ are as defined above and $H^+$ is a strong acid such as hydrochloric, hydrobromic, hydriodic, nitric, sulfuric, phosphonic or chloroacetic acid. Preferably $H^+$ is hydrochloric or hydrobromic acid and $OH^-$ is a strong base such as sodium hydroxide or potassium hydroxide, preferably in an aqueous, aqueous-alcoholic or alcoholic solution. Preferably, the hydroylsis is run in the presence of a strong acid.

In the above reaction scheme the group R and $R^1$ are not directly involved in reaction step (a) between 1,3,5- tricarboalkoxymethylhexahydro-1,3,5-triazine and the acyl chloride. Groups R, $R^1$, $R^2$ or $R^3$ are not directly involved in reaction step (b between the) N-carboalkoxymethyl-N-chloromethyl amide reaction product of step (a) and the phosphite. Groups R, $R^1$, $R^2$ and $R^3$ are removed in reaction step (c) when the phosphonate reaction product of reaction step (is subjected b) to hydrolysis. Therefore, the nature of groups R, $R^1$, $R^2$ and $R^3$ is not critical, although groups which would interfere with reaction steps (a) and (b) are to be avoided.

The group "$C_1$-$C_4$ alkyl" encompasses methyl, ethyl, n-propyl, isopropyl, n-butyl, isobutyl, sec-butyl, and tert-butyl. The group "$C_1$-$C_6$ alkyl" encompasses the same radicals as $C_1$-$C_4$ alkyl plus the 6 pentyls and the 16 hexyls.

The term "aliphatic group" is used in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

Reaction step (a) preferably is run at a temperature between about 0° to about 150° C., more preferably between about 40° to about 110° C. and most preferably between about 75° to about 85° C. This reaction step can be run at atmospheric, sub-atmospheric or super-atmospheric pressure, preferably at atmospheric pressure. Preferably the reaction is run in a solvent for the acyl halide, such as ethylene dichloride, methylene chloride, tetrahydrofuran or toluene.

Three moles of the acyl halide are needed to react with one mole of the 1,3,5-tricarboalkoxymethylhexahydro-1,3,5-triazine. An excess of acyl halide can be used to insure complete reaction with the triazine. A large excess of the acyl halide can serve as a solvent in this reaction step. The solvent or any excess acyl halide can be removed to isolate the N-carboalkoxymethyl-N-chloromethyl amide of the acyl halide in high yields. However, this amide quickly degrades by hydrolysis and should be kept in an inert atmosphere if isolated. Most preferably no excess acyl halide is used.

In reaction step (b), most preferably about equal mole amounts of N-carboalkoxymethyl-N-halomethyl amide of the acyl halide and the phosphite are reacted. Less preferably, up to 2 mole excess can be used and least preferably up to a 10 mole excess can be used.

The reaction is exothermic and can be run at a temperature between about 0° to about 150° C., more preferably between about 40° to about 100° C.; most preferably between 75° to about 85° C.

No solvent is needed for the reaction, however, any inert solvent can be used, preferably the solvent having a boiling point between about 40° to about 100° C. Examples of such solvents are ethylene chloride, methylene chloride, tetrahydrofuran and toluene. The use of an inert solvent helps dissipate the heat of reaction. Any solvent used in this reaction step will be removed after completion of reaction step (c), so preferably it is one that can be removed by evaporation.

Alkali metal phosphites having the formula

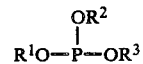

wherein $R^1$ and $R^2$ are as defined and $R^3$ is an alkali metal are reacted with N-cyanomethyl-N-halomethyl amide under an inert atmosphere such as nitrogen. The alkali metal phosphite can be prepared by reacting an alkali metal alkoxide, alkali metal hydride or alkali metal with an equal mole amount of a disubstituted phosphite of the formula

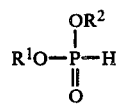

wherein $R^1$ and $R^2$ are as defined. This reaction is run in an inert atmosphere such as nitrogen.

Alkali metal phosphites of the formula

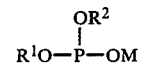

where $R^1$, $R^2$ and M are as defined can, becaue of tautomerism, have the following additional structural formula

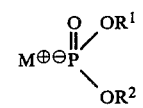

wherein $R^1$ and $R^2$ are as defined and M is an alkali metal.

In reaction step (c), a mole of the phosphonate reaction product from reaction step (b) is hydrolyzed with 5 moles of water. The hydrolysis is run in the presence of a strong acid or base as defined above. Preferably the hydrolysis is acid-catalyzed, preferably with an inorganic acid, and most preferably with hydrochloric or hydrobromic acid. The hydrolysis yields the desired N-phosphonomethylglycine. Preferably at least 2 moles of the acid are used. More preferably, a large excess over the 2 mole amount is used. The preferred hydrochloric or hydrobromic acid can be used in concentrated or aqueous form.

This last reaction step is run at a temperature between about 0° to about 200° C., preferably between about 50° to about 125° C. and most preferably between about 100° to about 125° C.

Atmospheric, sub-atmospheric or super-atmospheric pressure can be used. Preferably atmospheric pressure is used during the hydrolysis.

The solid N-phosphonomethylglycine can be recovered by conventional techniques in reaction step (c). Volatile liquid products such as alcohols (methanol) chlorides (methyl chloride), acids (acetic acid), water, and excess acid can be removed by standard stripping techniques. The desired N-phosphonomethylglycine is recovered in high purity by titurating it in isopropyl alcohol and removing it by filtration.

The process of this invention can be better understood by reference to the following specific examples.

EXAMPLE 1

Preparation of N-carboethoxymethyl N-chloromethyl acetamide

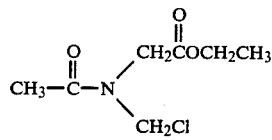

1,3,5-Tricarboethoxymethylhexahydro-1,3,5-triazine (5.76 grams, 0.0167 mole) was dissolved in 150 milliliters (ml) of 1,2-dichloroethane in a round-bottom flask. Acetyl chloride (5.4 ml, 0.074 mole) was added dropwise. The reaction mixture was refluxed 15 minutes, then stripped under reduced pressure to yield N-carboethoxymethyl-N-chloromethylacetamide. The structure was confirmed by proton nuclear magnetic resonance.

EXAMPLE 2

Preparation of O,O-dimethyl-N-carboethoxymethyl N-acetylaminomethyl phosphonate

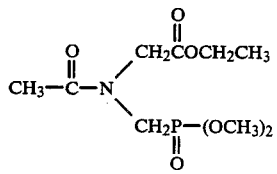

The amide compound prepared in Example 1 was diluted with 10-12 ml of toluene. Trimethylphosphite (6.7 g, 0.0515 mole) was added, and the mixture was refluxed 15 minutes, then stripped under reduced pressure to yield the desired product. The structure was confirmed by proton nuclear magnetic resonance.

EXAMPLE 3

Preparation of N-phosphonomethylglycine

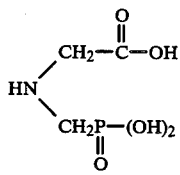

The phosphonate reaction product of Example 2 was combined with 30 ml (0.36 mole) of concentrated hydrochloric acid, refluxed 3 hours, and stripped under reduced pressure. The product was titurated in 50 ml of isopropyl alcohol and filtered to yield 5.6 g of the desired product. The structure was confirmed by proton nuclear magnetic resonance, $^{13}C$ nuclear magnetic resonance, infrared, and liquid chromatograph.

EXAMPLE 4

Preparation of O,O-diethyl-N-carboethoxymethyl-N-acetylaminomethyl phosphonate

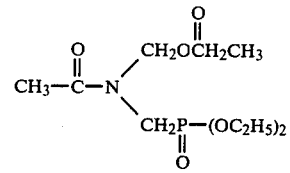

Three and nine-tenths grams (0.035 ml) of potassium-tbutoxide were slurried in a round bottom flask with 25 ml tetrahydrofuran (dried over molecular sieves) and the slurry was cooled in a water bath. Four and five-tenths ml (0.035 m) of diethyl phosphite were added dropwise over 5 minutes under nitrogen. This mixture was then cooled in an ice bath and 6.77 g (0.035 m) of N-carboethoxymethyl-Nchloromethylacetamide diluted with 25 ml of tetrahydrofuran were added dropwise over 15 minutes. The mixture was allowed to warm to ambient temperature and stirred 3 hours before it was filtered through dicalite and stripped to yield 9.6 g of an amber oil. Structure was confirmed by ir, nmr, ms, and C-13 nmr.

EXAMPLE 5

Preparation of N-phosphonomethylglycine

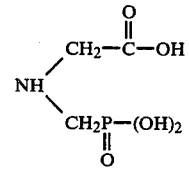

Six and six-tenths grams (0.022 m) of the compound obtained from Example 4 were combined with 30 ml (0.363 m) of concentrated HCl and refluxed 3 hours then stripped to yield 4.7 g of the desired product, a brown semi-solid. Structure was confirmed by $H^1$, nmr, C-13 nmr and lc techniques.

I claim:

1. A compound of the formula

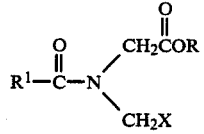

wherein R and $R^1$ are $C_1$-$C_4$ alkyl and X is chlorine, bromine or iodine.

2. The compound of claim 1 wherein R is ethyl, $R^1$ is methyl and X is chlorine.

3. The compound of claim 1 wherein R is ethyl, $R^1$ is ethyl and X is chlorine.

* * * * *